United States Patent [19]

Rosenbaum

[11] Patent Number: 5,084,036
[45] Date of Patent: Jan. 28, 1992

[54] DEVICE TO FACILITATE SELF-CATHETERIZATION IN WOMEN

[76] Inventor: Tomas P. Rosenbaum, 239 Riverside Garnet St., London E19 9SX, Great Britain

[21] Appl. No.: 572,931

[22] PCT Filed: Oct. 13, 1989

[86] PCT No.: PCT/GB89/01213
§ 371 Date: Sep. 6, 1990
§ 102(e) Date: Sep. 6, 1990

[87] PCT Pub. No.: WO90/04428
PCT Pub. Date: May 3, 1990

[30] Foreign Application Priority Data

Oct. 17, 1988 [GB] United Kingdom ............... 8824236

[51] Int. Cl.⁵ ..................... A61F 5/44; A61M 25/01
[52] U.S. Cl. ............................ 604/329; 604/330
[58] Field of Search ............... 128/3, 4, 15, 17, 9, 128/10, 11, 15, 16; 604/119, 103, 327–332

[56] References Cited

U.S. PATENT DOCUMENTS 4,690,677  9/1987  Erb ..................................... 604/329

FOREIGN PATENT DOCUMENTS 2137507 10/1984 United Kingdom .

Primary Examiner—Francis Jaworski
Assistant Examiner—Scott M. Akers
Attorney, Agent, or Firm—Reese Taylor

[57] ABSTRACT

A device is disclosed to facilitate self-catheterization in women who have an atonic bladder. The device comprises a body portion for insertion in the vagina, a locating member which lies substantially at right angles to the body portion and is intended to engage against the outside of the vagina, and a handle member on the locating member. The body portion has or is associated with a passageway one end of which is intended to engage against the mouth of the urethra and the other end of which is intended to receive the leading end of a catheter which can thus be guided into the urethra to facilitate self-catheterization. A locating and measuring device for use in the construction or selection of the self-catheterization device is also disclosed.

8 Claims, 2 Drawing Sheets

DEVICE TO FACILITATE SELF-CATHETERIZATION IN WOMEN

This invention relates to a device to facilitate self-catheterisation in women.

Persons who have a bladder or like sac which has become atonic, either spontaneously or iatrogenically, have to relieve the bladder by the insertion of a catheter through the urethra and into the bladder. This presents no problem for men but women, especially the elderly, arthritic or handicapped, experience some difficulty in locating the entrance to the urethra and in then inserting the catheter.

According to the present invention there is provided a device to facilitate self catheterisation in women, wherein a body portion for insertion in the vagina has or is associated with a passage way, one end of which is intended to engage against the mouth of the urethra and the other end of which is intended to receive the leading end of a catheter, and wherein the device incorporates a handle portion and a locating member which lies substantially at right angles to the body portion and is intended to engage against the outside of the vagina thereby to locate said one end of the passageway.

In the use of this device, the body portion is inserted into the vagina until the locating member abuts the outside of the vagina, whereby one end of the passageway is correctly located in relation to the mouth of the urethra. A catheter is then inserted into the passageway, the position of the other end of which can be readily determined, and then through the urethra to empty the bladder.

While the present device will generally be made in a relatively small number of standard sizes, both as regards width of the body portion and distance between the locating member and one end of the passageway, there may be occasions when the device has to be made to particular requirements, especially as regards the location of the said one end of the passageway, and, in any case, the distance between the locating member and the mouth of the urethra has to be measured. Accordingly, a subsidiary aspect of the present invention provides a locating and measuring device, comprising two body portions for insertion in a vagina, the leading ends of the body portions being hinged or elastically joined together, each body portion being connected at its other end to a locating member which lies substantially at right angles to the body portion, which is intended to engage against the outside of the vagina and which has a handle portion.

In the use of this latter device, the body portion is inserted into the vagina by the surgeon who then inserts a catheter into the urethra. The two handle portions are gripped by the surgeon to cause the body portions to clamp about the catheter, which together with the device is withdrawn and the distance between the locating members and the urethra is noted, this being the required distance between the locating member and the passageway in the final self-catheterisation device.

In order to enable the invention to be more readily understood, reference will now be made to the accompanying drawings, which illustrate diagrammatically and by way of example an embodiment thereof and in which.

Figure 1:
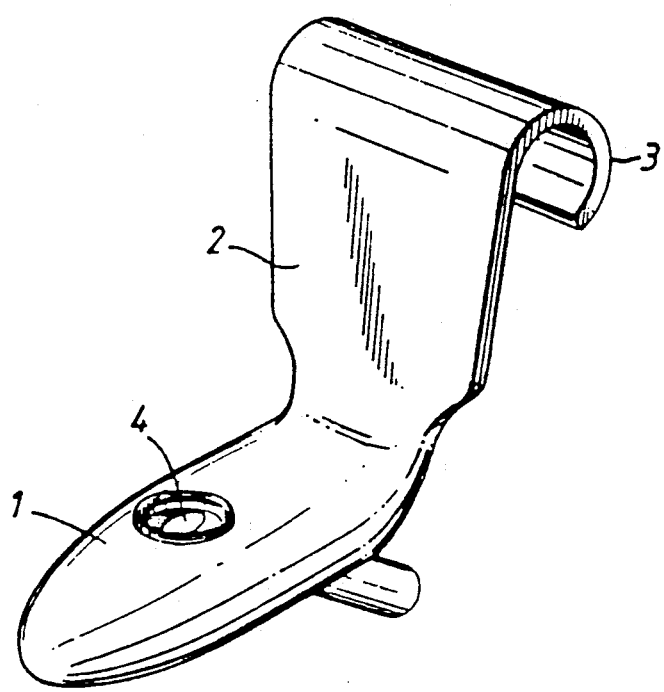
FIG. 1 is a perspective view of a device for facilitating self-catheterisation.
Figure 2:
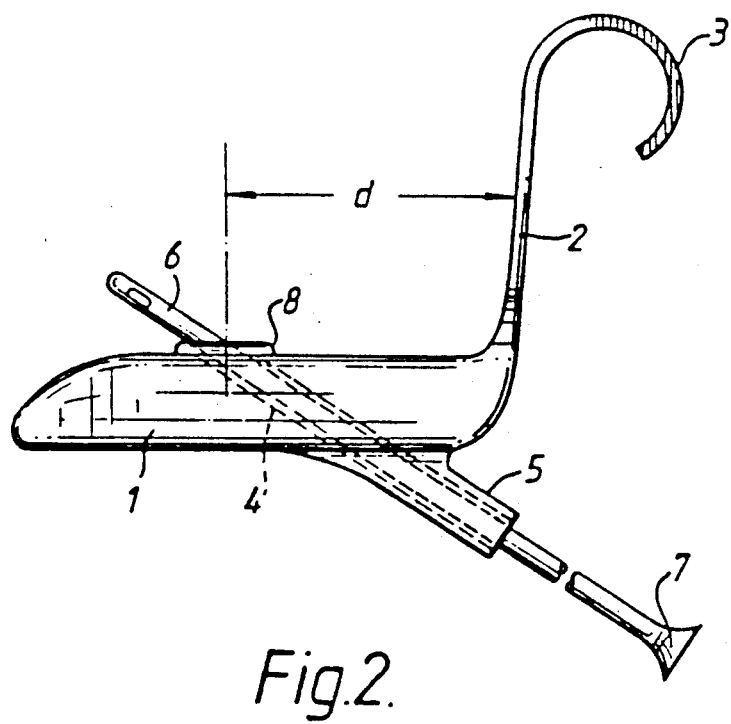
FIG. 2 is a side view of the device with a catheter in position.

Referring now to FIGS. 1 and 2 of the drawings, there is shown a device to facilitate self-catherisation in women for emptying the bladder. The device comprises a body portion 1, a locating member 2 substantially at right angles to the body portion and a handle portion 3 formed by curving the end of the locating member. The body member 1 is formed with a passageway 4 which extends in the form of a tube 5 below the body member.

In the use of the device, the body portion 1 is inserted into the vagina until the locating member 2 abuts against the outside of the vagina. In this position, the distance d is such that the mouth of the passageway 4 is located against the mouth of the urethra. A round-ended catheter 6 having a bell-shaped distal end 7 of a greater diameter than that of the tube 5, is then inserted through the tube 5 until its rounded end enters the bladder to allow drainage thereof. At the end of the drainage, the catheter is removed and then the device is removed and both are rinsed and stored for future use.

In order to facilitate the location of the mouth of the passageway 4 with the mouth of the urethra, the mouth of the passageway may be surrounded by a circular ridge 8. Because the end 7 of the catheter is of greater diameter than the passageway 4 or the tube 5, the catheter, if left in place, will automatically be removed when the device itself is removed.

Figure 3:
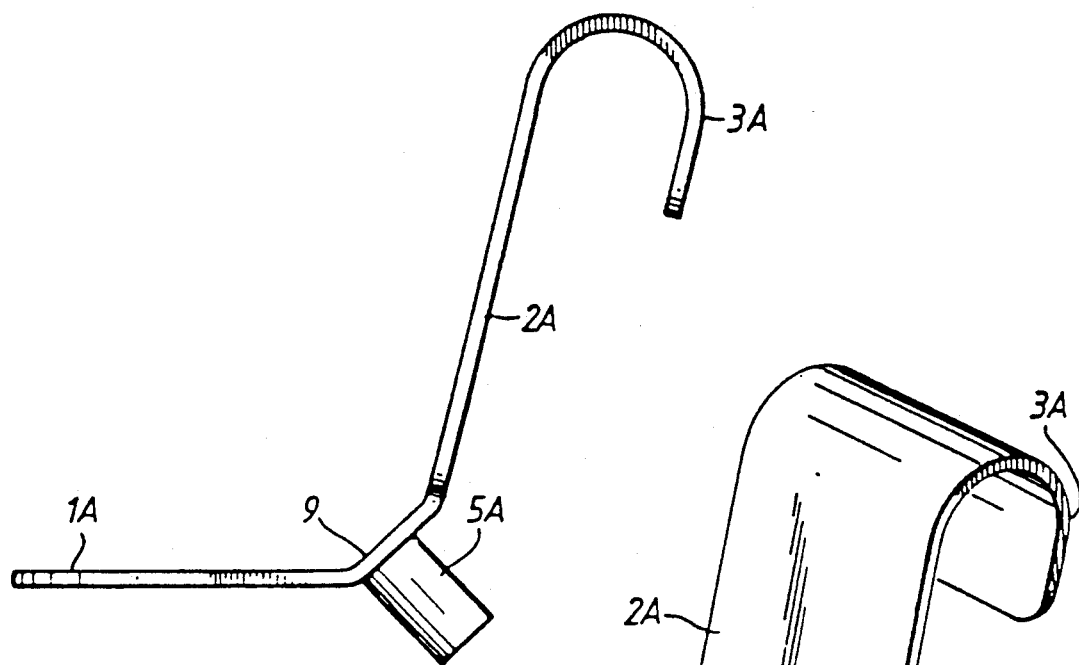
FIG. 3 is a side view of another form of the device for facilitating self-catheterisation.
Figure 4:
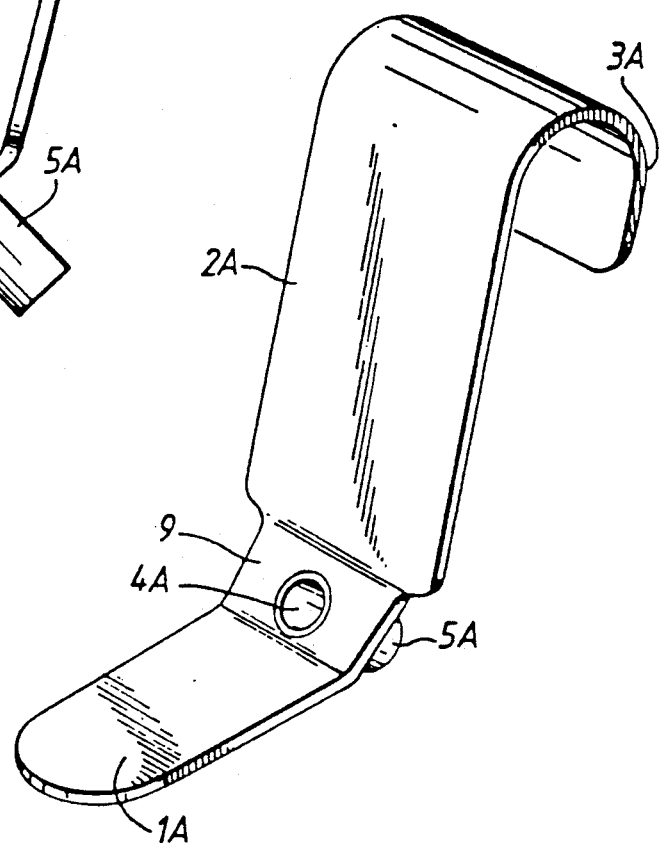
FIG. 4 is a perspective view of the device shown in FIG. 3.

FIGS. 3 and 4 show another form of the present device for facilitating self-catheterisation. This form of the device is simple to construct and may be suitable for use in most cases of atonic bladder. However, for special cases or where anatomical problems dictate, the more sophisticated device of FIGS. 1 and 2 will be preferred. The device shown in FIGS. 3 and 4 has its body portion 1A, locating member 2A and handle 3A formed from sheet plastics material with a tube 5A to receive a catheter, welded into a transition region 9 between the body portion and locating member.

The device is conveniently made of a plastics material, such as an acrylate plastics, which can be readily cleaned and subjected to physical or chemical sterilization procedures. It is desirable that the device should have no sharp corners, either internal or external, or re-entrant regions in which dirt and bacteria can accumulate. The device may be made as a solid body or the body portion can be formed by bending a sheet of plastics and welding a tube in an appropriate position, as shown in FIGS. 3 and 4.

It will be appreciated that modifications of the device just described are possible and the shape of the device may differ somewhat from that shown. Although the tube 5 is shown as an integral extension of the passageway 4, a construction is possible in which a separate tube is attached to or clipped into an appropriately shaped body portion. Alternatively, a separate lining may be provided for the passageway and tube. These modifications are particularly useful where the device is used with a sterile disposable catheter, since in these cases the separate tube or the lining can be provided sterile together with the catheter and discarded with the latter after use.

Figure 5:
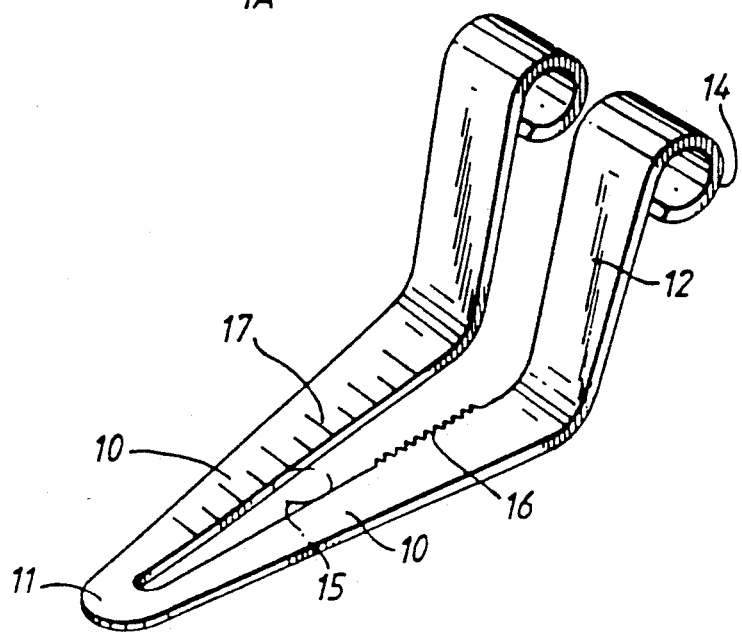
FIG. 5 is a perspective view of a locating device.

It is contemplated that the device will be available in at least two widths of the body portion for younger and older women and, for the device shown in FIGS. 1 and 2, at least three different lengths for the dimension d. However, in some cases it may be necessary to provide non-standard devices and, in any case, it will be necessary to measure the distance d so as to determine the appropriate size of device to use. FIG. 5 shows a device for measuring the distance d and thus locating the position of the mouth of the passageway in the device shown in FIGS. 1 and 2.

The device shown in FIG. 5 comprises two body portions 10 which are connected together at one end 11. The device is made of plastics which has a good degree of elasticity so that the two body portions 10 can be moved towards and away from each other, thereby effectively pivoting about the end 11. Each body portion 10 merges into a locating member 12 extending substantially at right angles to the body portion 10, and each locating member 12 terminates in a curved handle portion 14 by which the device can be held.

In the use of this device, the surgeon inserts the body members into the vagina of a patient and then inserts a catheter into the mouth of the urethra to locate the latter, while ensuring that the catheter is inserted between the body portions 10. If it has not already been inserted to its full depth, the device is then inserted until the members 12 abut against the outside of the vagina. The handle portions are then gripped and moved towards each other, thereby pivoting the body portions 10 which clamp the catheter, the position of which is indicated at 15, between them. The device and catheter are then retracted, making sure that the catheter is still firmly held between the body portions 10, whereupon the distance d (FIG. 2) can be measured and the appropriate self-catheterisation device prescribed or, if necessary, made to measure.

If desired, the inside edges of the body portions 10 can be serrated or roughened as indicated at 16 to improve the grip on the catheter and the body portions 40 can be provided with an appropriate scale 17.

The present self-catheterisation device is a cheap and simple device which makes it easy for women, especially those who are infirm, arthritic or handicapped, to effect self-catheterisation where this is necessary for drainage of an atonic bladder in a more elegant, hygienic and less traumatic manner than theretofore.

I claim:

1. A device to facilitate self-catheterization in women, comprising:
    a) a body portion for insertion into the vagina and having a top and bottom surface and a longitudinal axis a through passageway disposed at an acute angle to said longitudinal axis one end of which is adapted to engage the mouth of the urethra at the top surface and the other end, having means for receiving the end of a catheter; and
    b) a locating member extending at substantially right angles from the top surface of said body portion and adapted to engage the outside of the vagina whereby said one end of said passageway is positioned at the mouth of the urethra when said body portion is positioned within the vagina.

2. The device of claim 1 wherein a handle portion extends from said locating member.

3. The device of claim 1 or 2 wherein the device consists of plastic material.

4. The device of claim 1 or 2 wherein said body portion and said locating member comprise a unitary molded member having a through passageway in said body portion.

5. The device of claim 1 or 2 wherein a hollow tube is secured to said body portion coaxially with respect to said passageway and in communication with said other end thereof and extending thereform.

6. The device of claim 1 or 2 wherein a raised ridge is provided on said body portion adjacent said one end of said passageway.

7. The device of claim 1 wherein the catheter is a round-ended catheter having a bell-shaped distal end of a diameter greater than the diameter of said passageway.

8. The device of claim 5 further comprising a catheter inserted in said passage wherein the catheter is a round-ended catheter having a bell-shaped distal end of a diameter greater than the diameter of said hollow tube.

* * * * *